United States Patent
Wulc et al.

(10) Patent No.: US 7,060,079 B2
(45) Date of Patent: Jun. 13, 2006

(54) SURGICAL INSTRUMENT FOR ENDOSCOPIC SUTURING OF DEEP SUBCUTANEOUS TISSUE

(75) Inventors: Allan E. Wulc, Abington, PA (US); Stanley S. Wulc, Jamison, PA (US)

(73) Assignee: Eye Plastic Surgery, Ltd., Abington, PA (US)

( * ) Notice: Subject to any disclaimer, the term of this patent is extended or adjusted under 35 U.S.C. 154(b) by 107 days.

(21) Appl. No.: 10/336,277

(22) Filed: Jan. 3, 2003

(65) Prior Publication Data

US 2004/0133216 A1   Jul. 8, 2004

(51) Int. Cl.
*A61B 17/04* (2006.01)

(52) U.S. Cl. ............... 606/148; 606/144; 606/1
(58) Field of Classification Search ........... 606/139, 606/144, 148
See application file for complete search history.

(56) References Cited

U.S. PATENT DOCUMENTS

| | | | | |
|---|---|---|---|---|
| 4,841,888 A | * | 6/1989 | Mills et al. | 112/169 |
| 5,507,754 A | * | 4/1996 | Green et al. | 606/139 |
| 5,549,617 A | * | 8/1996 | Green et al. | 606/144 |
| 5,792,153 A | * | 8/1998 | Swain et al. | 606/144 |
| 5,797,927 A | * | 8/1998 | Yoon | 606/144 |
| 5,871,490 A | | 2/1999 | Schulze et al. | |
| 5,947,982 A | | 9/1999 | Duran | |
| 5,980,538 A | | 11/1999 | Fuchs et al. | |
| 5,984,932 A | * | 11/1999 | Yoon | 606/147 |
| 6,036,700 A | | 3/2000 | Stefanchik et al. | |
| 6,533,796 B1 | * | 3/2003 | Sauer et al. | 606/144 |

\* cited by examiner

*Primary Examiner*—Glenn K. Dawson
*Assistant Examiner*—Darwin P. Erezo
(74) *Attorney, Agent, or Firm*—Paul & Paul

(57) ABSTRACT

A surgical instrument is provided, principally for use with endoscopic plastic surgery, and adapted for insertion into an incision for engaging subcutaneous tissue, fat, fascia or muscle (STFFM) through a remote access incision, grasping the STFFM, and enabling it to be moved to another location. The STFFM is grasped preferably by engaging it with a needle and passing a suture through it, with the suture being locked by engagement via a hook, all at a location inside the skin that is remote from the opening. This enables the sutured STFFM to be moved, in any direction, but most often toward the incision as the inserted portion of the instrument is removed. A vacuum and an external clamp are provided, for facilitating engagement of the portion of the STFFM that is to be sutured. The instrument is usable for facelift surgery midface surgery, brow surgery, neck lift, scalp reduction, endoscopic mastopexy, endoscopic thigh lift, endoscopic tummy tuck, and for any other technique where it is desired to shift STFFM from one location to another location, as for example, in the correction of undesirable liposuction results.

21 Claims, 9 Drawing Sheets

SURGICAL INSTRUMENT FOR ENDOSCOPIC SUTURING OF DEEP SUBCUTANEOUS TISSUE

BACKGROUND OF THE INVENTION

Endoscopic surgery has evolved such that many operations are being performed through incisions of ever-decreasing size. Endoscopic surgery classically can be performed with incisions as small as 4 mm. The greatest limitations in performing endoscopic surgery through an incision of this size is the difficulty of engaging tissue and passing sutures to a location remote from the access point to a remote location under the surface of the skin. While some surgeons develop the manual dexterity and experience to effectively suture tissue at the internal location remote from the incision, very few techniques have been developed to deal with this problem effectively.

Often surgeons are forced to make additional incisions, simply because of the difficulty of needle passage. For example, in performing an endoscopic facelift, the surgeon is often forced to place an incision inside the mouth or through the desired location in the skin surface. They are also obliged to widely undermine (make large internal incisions) to clear enough space within the internal space viewed by endoscopy to allow the instrumentation in that is to pass and then retrieve the needle. With manual remote access techniques, often a significant amount of skin must be (lifted) undermined from the underlying fascia, fat and musculature to allow room to maneuver an endoscope, a needle holder, and the grasping forceps. Often 4 hands are necessary (surgeon+assistant) to hold the instrumentation and pass the needle.

The limitations of currently available techniques as discussed above produce certain potential surgical risks including needle breakage within the face, needle loss within the face, injury to the facial nerve, its branches, sensory nerves, and blood vessels, dimpling in the skin, improper needle location, inability to pass the suture to obtain the desired lifting effect, as well as the need to open the area completely to retrieve a lost needle or for repair of nerves or vessels.

SUMMARY OF INVENTION

The present invention is directed to providing an instrument for endoscopically surgically engaging and grasping the deep surface of the skin, fascia, fat, or muscle of a patient. This allows the suture to be employed to engage and lift the grasped tissue such that it can be sutured to stable supporting tissue in order to obtain a suture "lift" of the deep tissue along with the skin. An endoscopic instrument is inserted into the opening, preferably carrying a suture. Preferably, vacuum is applied through the instrument for engaging the skin, muscle, fat, fascia, or other subcutaneous tissue at a precise location that is determined by turning on the vacuum in the instrument and gauging, and refining vacuum placement so that the optimum vector of lift and thus the optimum location of suture placement is verified. Preferably, an external clamp is then placed over the exterior surface of the skin to assist the vacuum engagement of the skin and to verify the location inside the tissue that is sutured, due to visual placement of the clamp on the external surface of the skin. A straight needle then passes through the suction apparatus, carrying the suture as it passes through the skin that is to be engaged. Preferably, a hook carried by the instrument then hooks the suture that has been passed through the deep tissue. The hooked suture, passed through the deep tissue, may then be withdrawn as the instrument is withdrawn.

Accordingly, it is an object of this invention to provide a remote access endoscopic suture passer.

It is another object of the present invention to provide an instrument for endoscopically surgically engaging and grasping the deep subcutaneous tissue, fascia, fat, or muscle of a patient internally and remote from a skin access opening in order to engage the grasped tissues and skin relative to the opening.

It is a further object of this invention to accomplish the above object, wherein the deep subcutaneous tissue, fascia, fat, or muscle that is engaged and grasped is sutured with a needle, and with the suture being hooked to the instrument such that the engaged and sutured deep subcutaneous tissue, fascia, fat, or muscle may be moved toward the access opening of the skin as the instrument is withdrawn through that opening.

It is another object of this invention to facilitate suturing of the deep subcutaneous tissue, fascia, fat, or muscle via a vacuum delivery through the instrument, such that the vacuum is used to engage the tissues internally in order to facilitate suturing the deep subcutaneous tissue, fascia, fat, or muscle. The object of the vacuum within this instrument is to allow assessment of optimum suture placement such that the desired vector or lift can be achieved without creating dimpling or an unnatural look. Furthermore, the vacuum is used to facilitate needle passage.

It is a further object of this invention to accomplish the above objects, wherein a clamp is applied to the outside of the skin, just outside the location where the inside tissue is to be sutured, in order to facilitate the engagement of the inside portion of the deep subcutaneous tissue, fascia, fat, or muscle that is to be sutured.

It is another object of this invention to accomplish the above objects for facilitating all aesthetic surgery including facelifts, brow surgery, breast lifts, thigh lifts, abdominal lifts, skin deep subcutaneous tissue, fascia, fat, or muscle shifting from one location to another, and deep suturing of flaps.

It is another object of this invention to accomplish suturing of this sort in deep subcutaneous tissue, fascia, fat, or muscle in endoscopic procedures including general surgery, laparoscopic obstetric and gynecologic surgery, and in arthroscopic orthopedic and podiatric surgery.

It is another object to provide an enclosed system for suture passage that is self-retrieving, without the need for regrasping and/or a protected needle enclosed within a system.

It is another object of the invention to use vacuum on the STFFM as a localization system in order to decide exactly where the optimum vector of lifting is to occur.

It is a further object of this invention to provide an alternative to the external device and/or vacuum application, to be applied through the use of a toothed forceps for internally grasping the subcutaneous tissue, fat, fascia, or muscle in lieu of, or in addition to, the above proposed mechanisms.

Other objects and advantages of the present invention will be readily understood upon a reading of the following brief descriptions of the drawing figures, the detailed descriptions of the preferred embodiments, and the appended claims.

BRIEF DESCRIPTIONS OF THE DRAWING FIGURES

Figure 2:
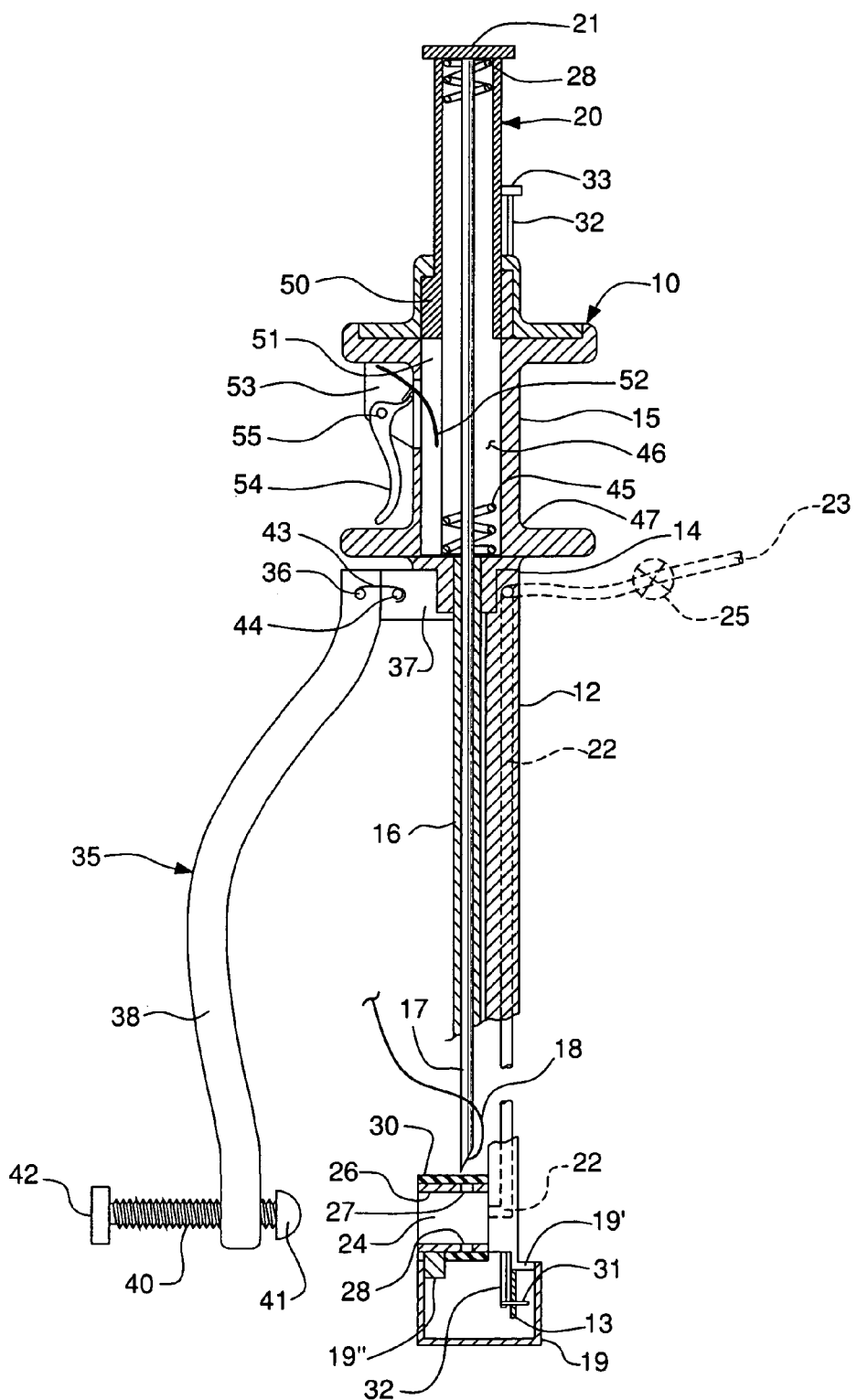
FIG. 2 is a vertical sectional view through the instrument of FIG. 1, wherein the instrument is shown in the needle withdrawn position, and wherein the various operative components of the instrument are illustrated.
Figure 2A:
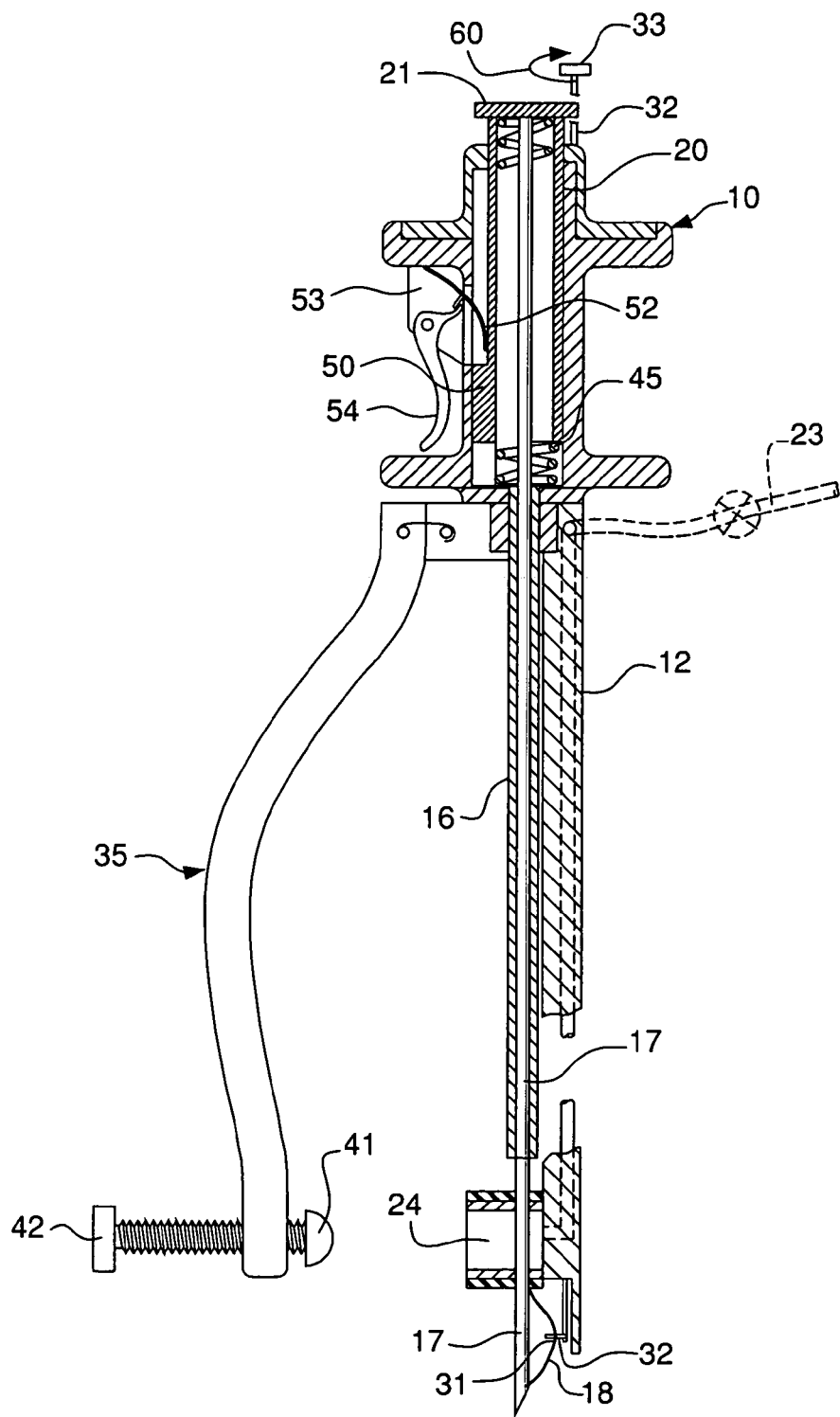
FIG. 2a is a view similar to that of FIG. 2, but wherein the suturing needle is shown in the "down" or engaged position, such that the suture carried thereby can be "hooked".
Figure 3A:
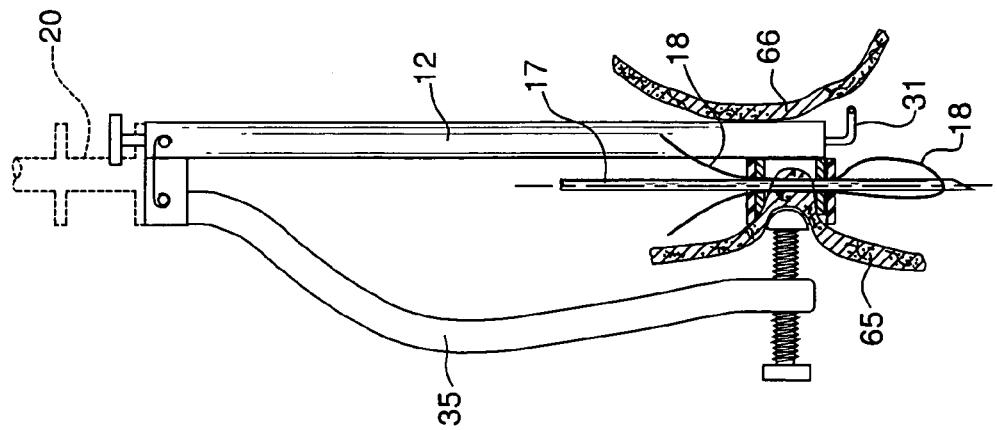

FIG. 3a is a schematic view of a portion of the instrument of FIGS. 2 and 2a, in which the suturing needle is in the "up" position, with the instrument is disposed between inner and outer surfaces between the skin and soft tissue of a patient, with vacuum applied to a cavity at the lower end of the instrument, drawing the skin subcutaneous tissue, fat, fascia or muscle (hereinafter abbreviated STFFM) into the cavity, and with a clamp applied to the outer surface of the skin also effecting engagement of the STFFM that is to be sutured into the cavity, and with the suturing needle in the "up" position.

Figure 3B:
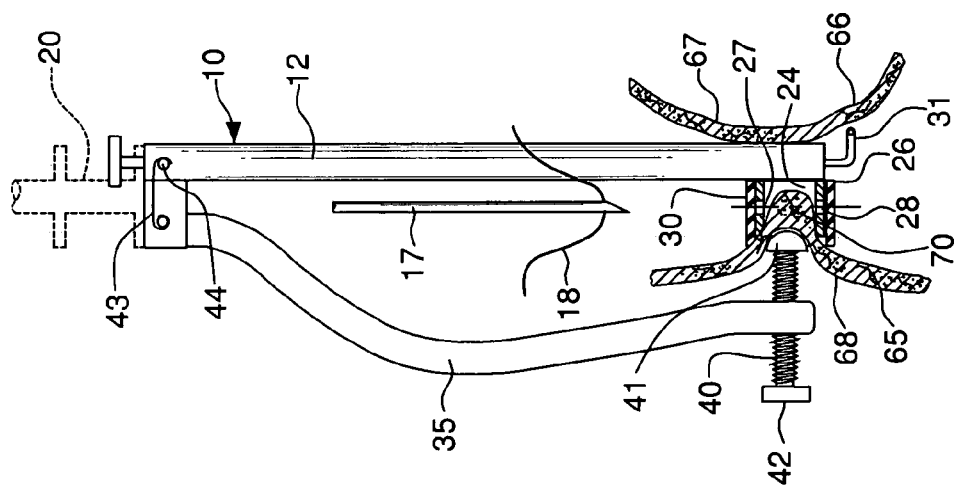

FIG. 3b is an illustration like that of FIG. 3a, wherein an elastomeric sleeve is shown over the cylindrical sleeve and with the STFFM disposed in the cavity.

Figure 3C:
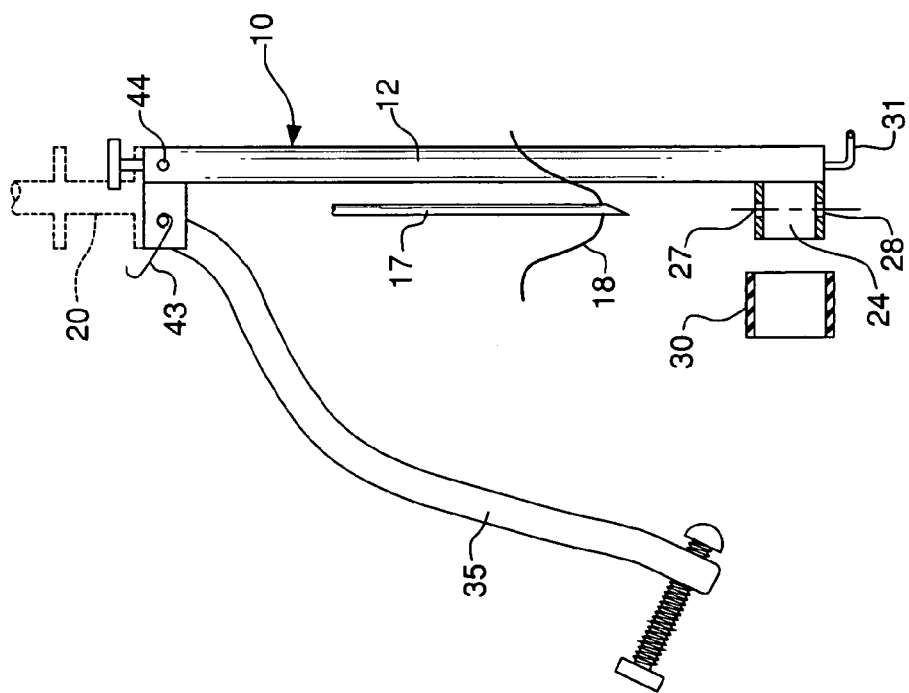

FIG. 3c is an illustration like that of FIG. 3b, but wherein the suturing needle is applied through the cavity, through the STFFM that is to be sutured, carrying the suture therethrough.

Figure 3E:
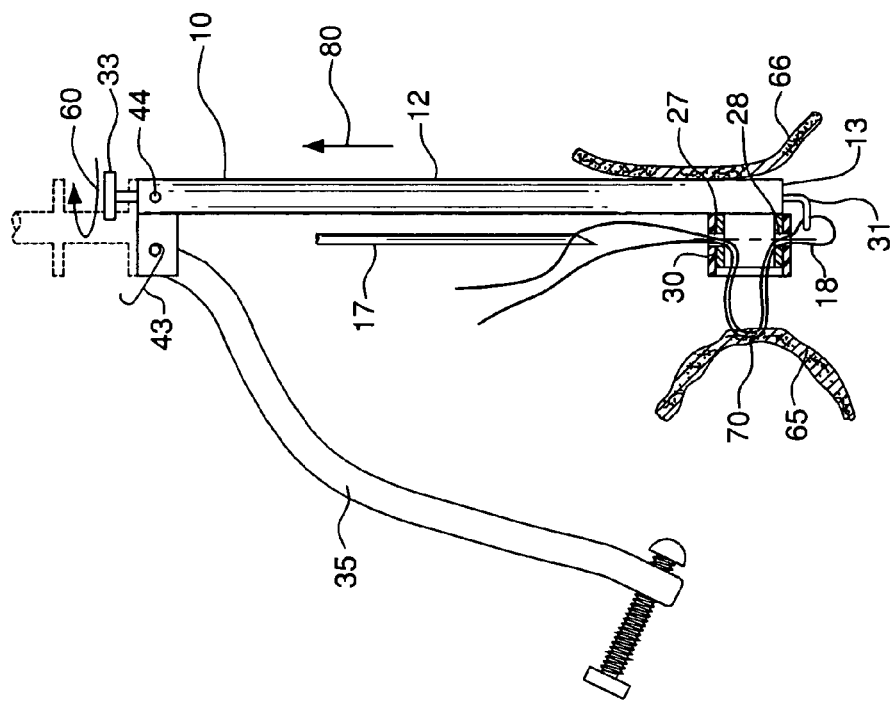
Figure 3D:
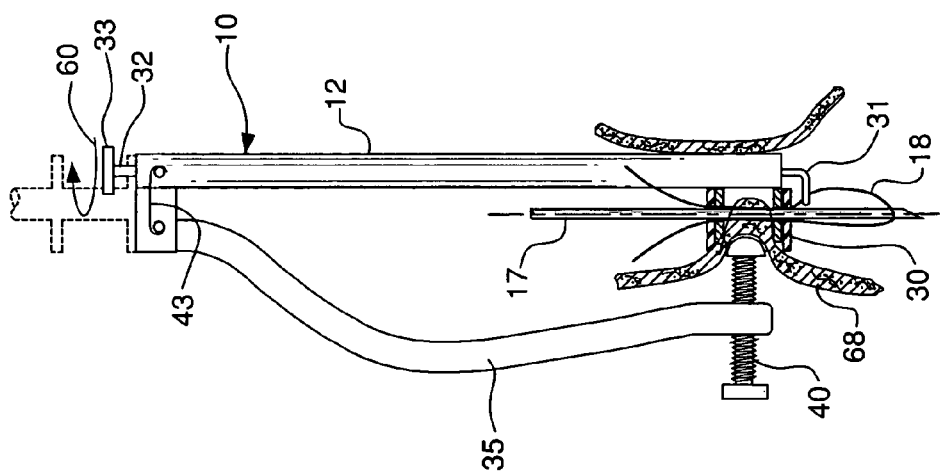

FIG. 3d is an illustration like that of FIG. 3c, but wherein a manually actuable hook carried at the lower end of the instrument is turned from above, to engage and hook the suture that has been passed through the cavity and engaged STFFM.

FIG. 3e is an illustration like that of FIG. 3d, but wherein the clamp is removed, the suturing needle is in the "up" or withdrawn position, and wherein the sutured STFFM is shown attached to the cavity by means of the suture that has been hooked by the hook at the lower end of the instrument, such that, withdrawal of the instrument will withdraw the sutured STFFM in the direction of withdrawal.

Figure 4A:
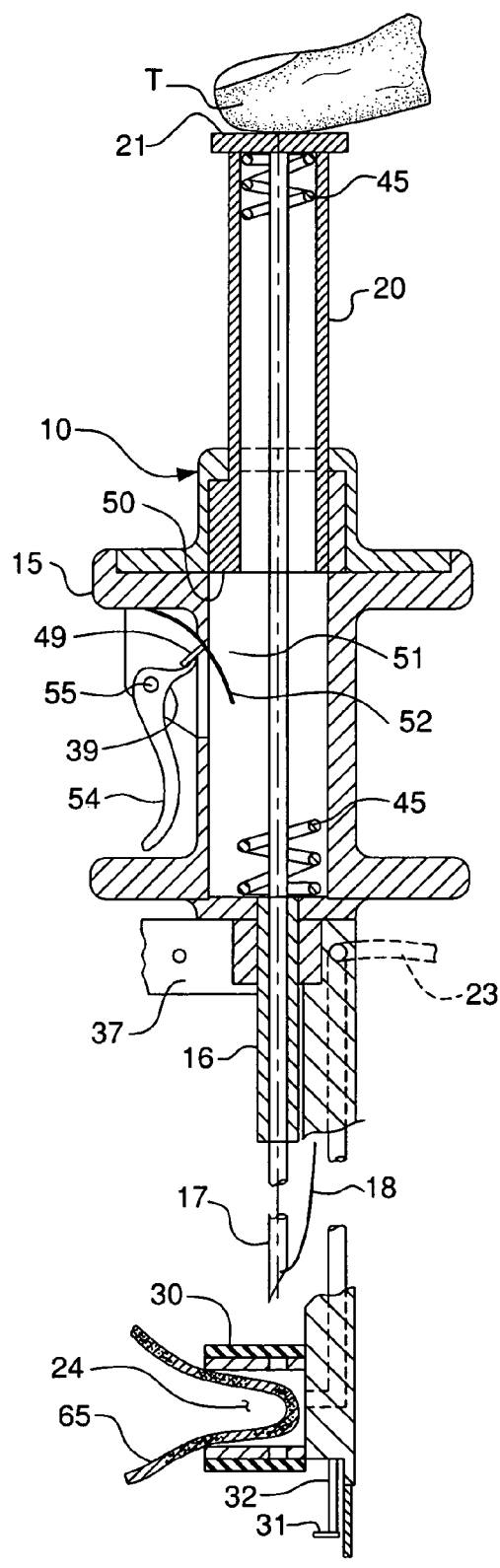

FIG. 4a is a vertical sectional split view, fragmentally illustrating a different portion of the operation of the instrument, whereby the surgeon is poised to depress the upper end of the plunger to drive the needle through the STFFM in the cavity, in a downward direction.

Figure 4B:
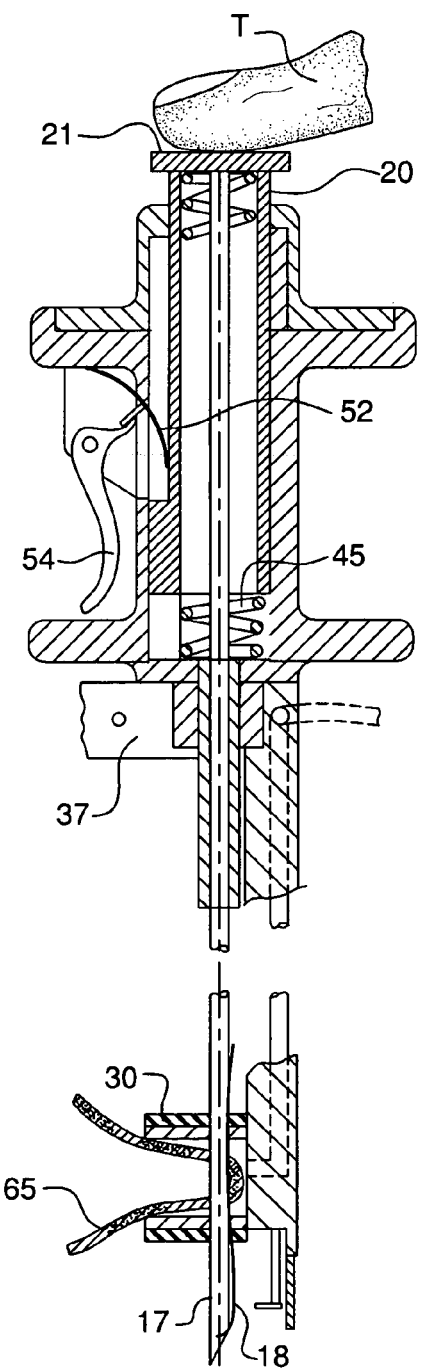

FIG. 4b is an illustration like that of FIG. 4a, but wherein the thumb of the surgeon has depressed the plunger completely downwardly, and wherein the needle has passed through the STFFM in the cavity, pulling the suture through the STFFM and cavity along therewith.

Figure 4C:
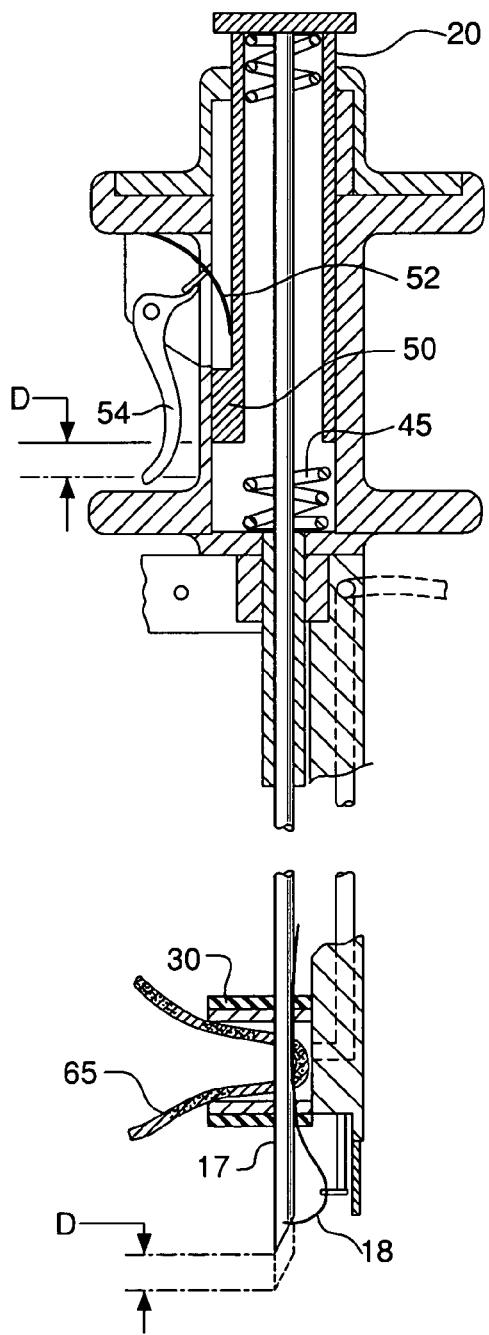

FIG. 4c is an illustration like that of FIGS. 4a and 4b, but wherein the thumb of the surgeon has been withdrawn from the upper end of the plunger, allowing the compression spring to urge the plunger upwardly a distance "D", whereupon the lower end of the needle is withdrawn upwardly along therewith, such that a loop is formed in the suture that may be grasped by a hook at the lower end of the instrument.

Figure 4D:
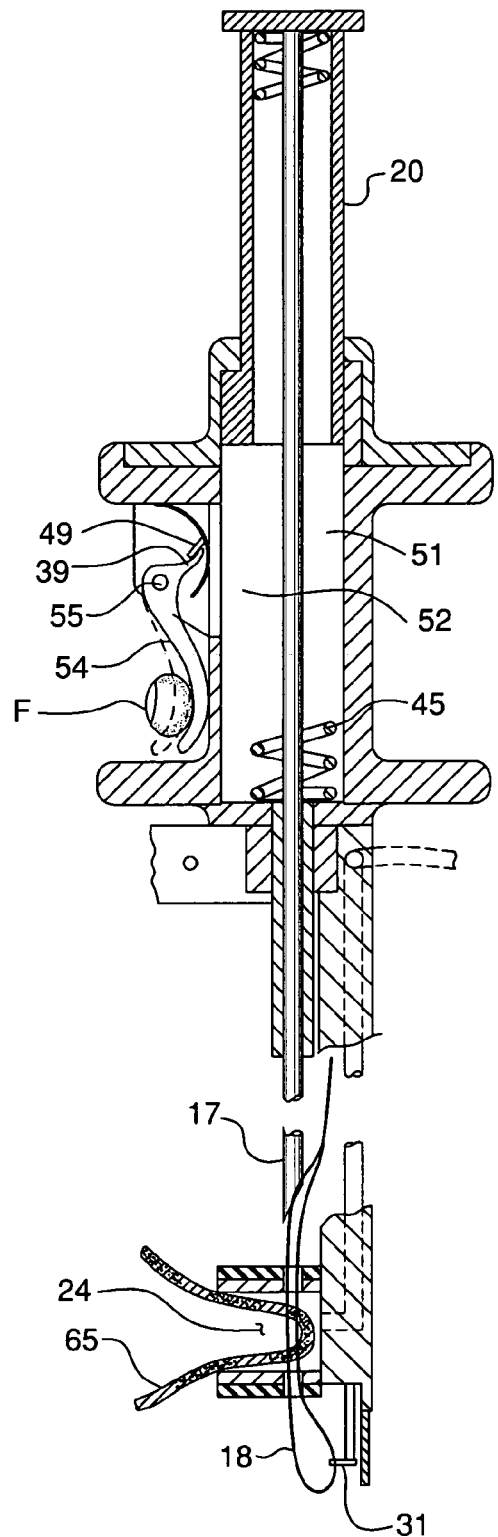

FIG. 4d is an illustration like that of FIG. 4c, but wherein the forefinger of the surgeon has been applied to the lever, to retract the lever spring from the position therefore shown in phantom in FIG. 4d, to that of the full line position shown in FIG. 4d, such that the compression spring can drive the plunger upwardly to the position shown in FIG. 4d, leaving the suture secured through the STFFM and cavity of the instrument due to the hooked engagement of the suture at the lower end of FIG. 4d.

Figure 5:
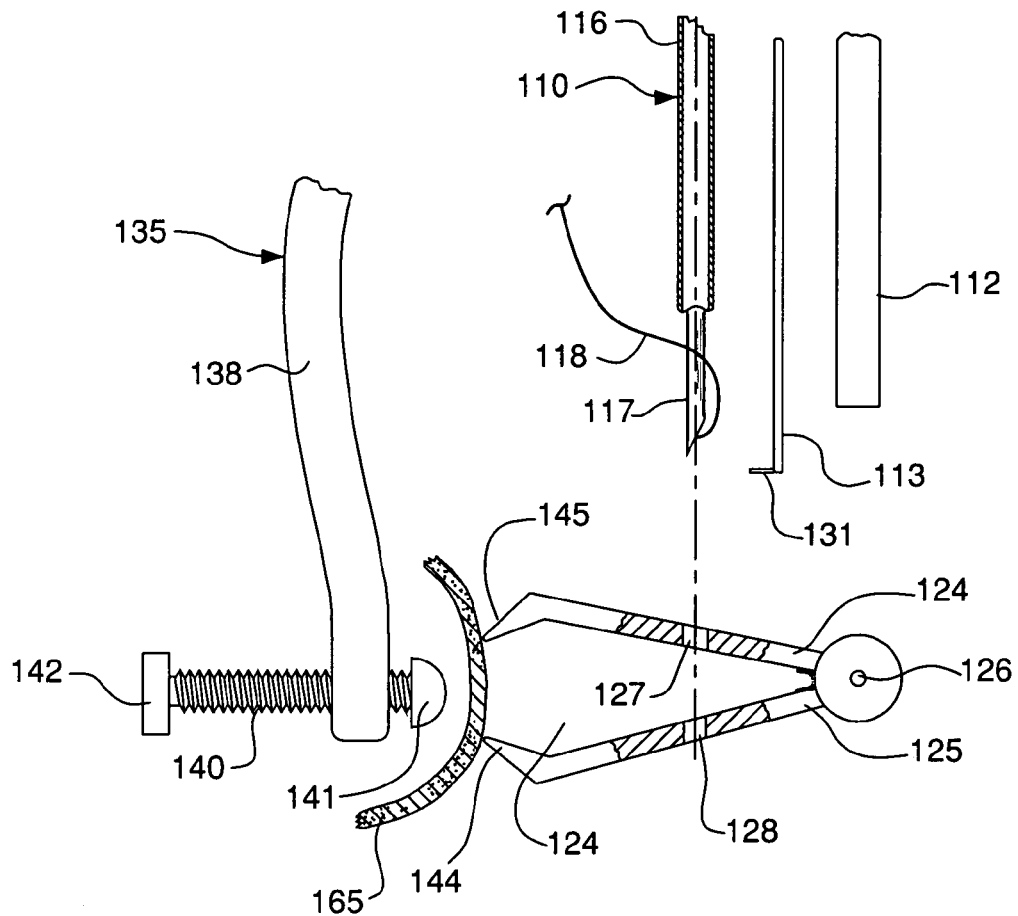

FIG. 5 is a fragmentary view of an alternative embodiment to the instrument of FIG. 2.

Figure 5A:
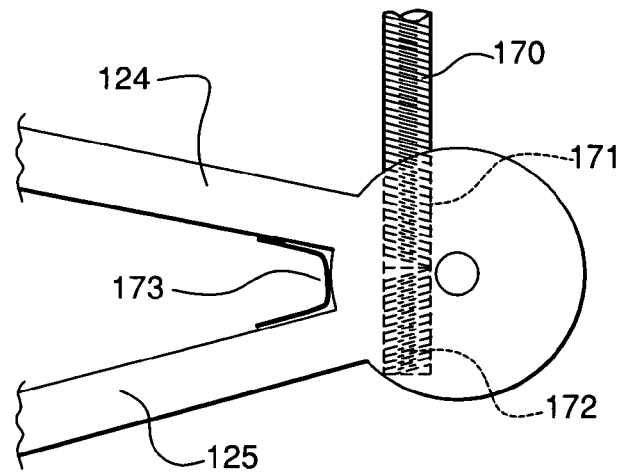

FIG. 5a is an enlarged fragmentary detailed view of a mechanism for opening and closing the internal toothed forceps of the embodiment of FIG. 5.

Figure 6:
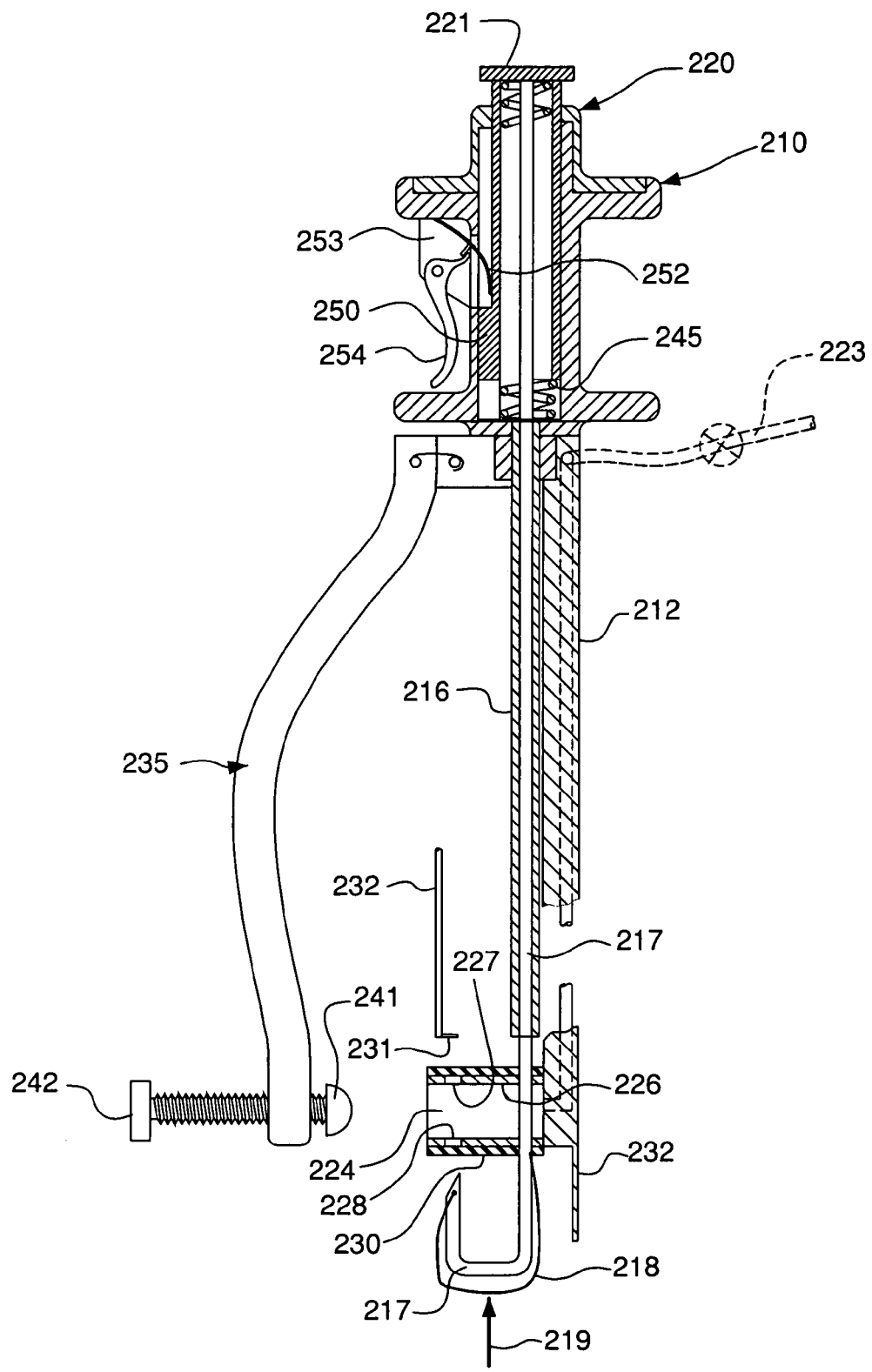

FIG. 6 is another alternative embodiment of the instrument of this invention.

DETAILED DESCRIPTIONS OF THE PREFERRED EMBODIMENTS

Figure 1:
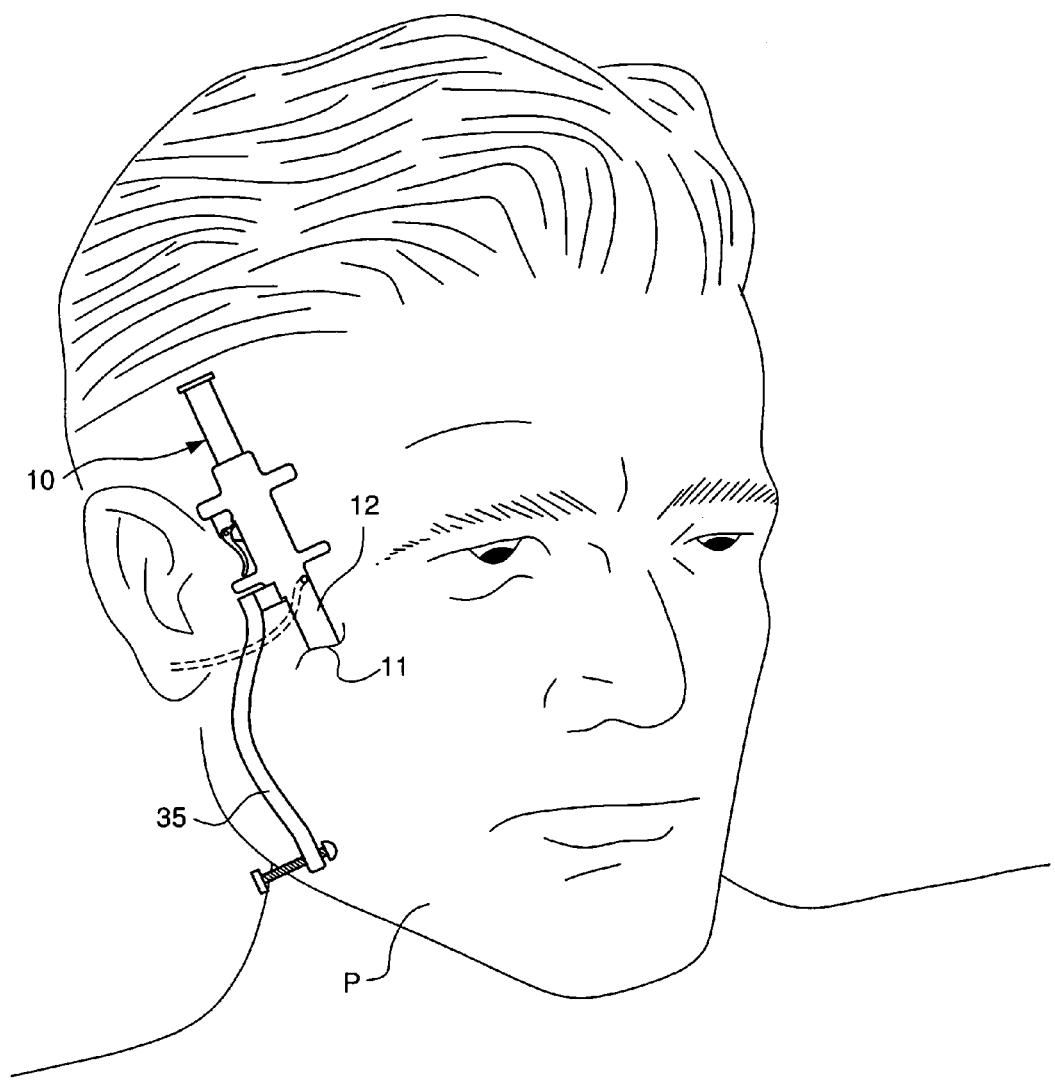
FIG. 1 is an illustration of the instrument of this invention being applied through an access opening in the face of a patient, as it would be for effecting a facelift in a patient.

Referring now to the drawings in detail, reference is first made to FIG. 1, wherein an instrument 10 is shown in an incision or opening 11 in the skin of a patient P, in accordance with this invention, wherein the instrument 10 is being used during a facelift operation.

With reference to FIG. 2, it will be shown that the instrument 10 includes an insert 12 having first and second ends 13 and 14, respectively. Above the upper or second end 14 of the insert 12, there is a manually graspable portion of the instrument 10, shown in the shape of a spool 15, which portion 15 of the instrument remains outside the incision or access opening 11 of the patient, during use. Portions of the insert 12 near the lower end are shown broken away for the sake of clarity. The insert 12 includes a hollow sleeve 16 extending downwardly from the lower end of the spool 15. A suturing needle 17 is slideably carried in the sleeve 16, for upward and downward movement therein, with the needle 17 carrying a suture 18 at its lower end, which suture 18 enters into the skin access opening 11 with the instrument 10, as the insert portion 12 of the instrument 10 passes into the opening 11. The upper end of the needle 17 is carried by a vertically moveable plunger 20, being mounted to the upper end 21 of the plunger, for movement therewith, as the plunger 20 is engaged by the surgeon for downward movement thereof from the position of the plunger 20 illustrated in FIG. 2.

The insert 12 also carries a vacuum conduit 22 therethrough, extending downwardly from a vacuum line 23 down to a leftwardly opening cavity 24, as shown in FIG. 2. A manually actuable valve 25 is provided for the vacuum line 23, for on/off actuation by the surgeon. The cavity 24 is comprised of cylindrical sleeve 26 having upper and lower needle-passing holes 27 and 28 respectively in vertical alignment relative to each other, as shown in FIG. 2, for passage of the lower end of the needle 17 therethrough, when the needle 17 is actuated by the surgeon to pass through the cavity 24.

A rubber, neoprene or similar sealing cylindrical sleeve 30 is applied over the sleeve 26, with the sleeve 30 having no holes therethrough, to facilitate a sealing adherence to the exterior of the needle 17 after the needle 17 is passed through the cavity 24, via the openings 27, 28, to facilitate maintaining a vacuum on STFFM that is engaged in the cavity 24. A hook 31 is shown at the lower end of the insert 12, carried by a vertically disposed rod 32, which rod 32 extends from the first end 13 of the insert 12, up through the insert (not shown), passing through the instrument 10, to emerge at the upper end thereof, and terminating in an actuation knob 32.

With reference to FIG. 2 it will be seen that a safety cap 19 is provided, carried in snap-on, snap-off relation by bosses 19', 19", that, in turn, are carried by the insert 12 and sleeve 26, with the boss 19" projecting through the sealing cylindrical sleeve 30, as shown, such that the cap 19 provides protection for the hook 31 as shown in FIG. 2, as well as providing protection for the needle 17 after it is inserted through the cavity 24. Additionally, the removable cap 19 protects the patient when the instrument 10 is inserted beneath the skin of a patient as described below with respect to FIGS. 3a–e, FIGS. 4a–d and FIG. 6. Thus, the patient is protected from the needle stroke and the loop of the suture 18 is protected from being distorted by tissue engagement. Additionally, the use of the cap 19 facilitates retrieval of the suture via the hook. Additionally, accidental breakage of the needle 17 is minimized.

The safety cap 19 illustrated in FIG. 2, is not specifically illustrated in FIGS. 3a–e, FIGS. 4a–d and FIGS. 5 and 5a, in the interest of clarity, for emphasizing other components of the instruments of this invention, but it will be understand that the safety cap 19 is similarly carried at the lower end of the instruments of these other above-mentioned Figures.

An external clamp device 35, is shown in FIG. 2, pivotally mounted at 36, to a boss 37 at the upper end of the insert 12, below the spool 15. The clamp device 35 includes a clamp rod 38 carried by the boss 37 at its upper end, and which carries a threaded member 40 at its lower end. The member 40 has an exterior skin-engaging contact 41, preferably of a soft material such as rubber, neoprene or the like, at its right end as shown in FIG. 2, and a manual actuation knob 42 at its left end. The rod 38 is pivotally moveable leftward from its position shown in FIG. 2 about pivot 36, but can be locked in the position shown in FIG. 2 via any suitable locking means, such as by means of a clasp 43 in hooked engagement over a keeper 44 carried by the boss 37, as shown.

A helical compression spring 45 is shown, disposed about the upper end of the needle 17, inside the spool 15, in seated engagement against the lower end 47 of the spool 15, and pressing against lower surface 28 of the upper end 21 of the plunger 20, although the intermediate portions of the spring 45 are shown broken away for the sake of clarity. The effect of the spring 45 is to urge the plunger 20 toward its upper position as shown in FIG. 2. When the plunger 20 is engaged at its upper exterior end 21 by the surgeon, for moving the needle 17 downwardly from the position shown in FIG. 2, to pass through the cavity 24 as aforesaid, the leftward protrusion 50 thereof, at the lower end of the plunger 20 can move vertically downwardly, sliding in keyway 51. As the protrusion 50 moves downward, it will engage the leaf spring 52 mounted on support member 53 and moves the spring 52 leftwardly as shown in the phantom position therefore illustrated in FIG. 4a.

With reference to FIG. 2a, it will be seen that the plunger 20 has been engaged at its upper end 21 and moved vertically downwardly, compressing the compression spring 45, lowering the needle 17 to its downward position as shown in FIG. 2a, with the lower end of the needle 17 and the suture 18 carried thereby in engagement through the cavity 24, having passed through holes 27, 28 (not shown in FIG. 2a), and with the sealing sleeve 30 being in sealed engagement against the exterior of the needle 24. The hook 31 carried by the rod 32, at the lower end of the insert 12, is shown in FIG. 2a as being in the hooked position, engaging the suture 18 upon the knob 33 at the upper end of the rod 32 having been manually engaged and turned in the direction of the arrow 60 shown in FIG. 2a.

Referring now to FIGS. 3a–3e, the use of the instrument of this invention will now be discussed.

In FIG. 3a the instrument 10 is shown, with the upper end, including the plunger 20 thereof being in phantom. The needle 17 which carries the suture 18 is shown, fragmentally illustrated, poised to descend through holes 27 and 28 of the cavity 24. The elastomeric sleeve 30 is shown to the left of the cavity 24, over which it is applied prior to insertion of the insert 12 into the incision 11 on the face of the patient P. In the illustration of FIG. 3a, the clamp device 35 is shown in the outward position, with the clasp 43 unclasped from the keeper 44, in order to facilitate insertion of the insert 12 into the skin opening 11.

With reference now to FIG. 3b, the insert 12 is shown inserted through the incision 11, between outer and inner skin layers 65, 66 respectively, with the right surface 67 of layer 66 representing the STFFM surface inside the patient P (such as inside the mouth of the patient), and with the left-most surface 68 of the skin layer 65 representing the outer surface of the face of the patient P. In the illustration of FIG. 3b, the elastomeric sleeve 30 is shown applied over the cylindrical sleeve 26, closing the holes 27, 28 thereof.

At this point, the valve 25 shown in FIG. 2 is actuated to provide vacuum via line 23, down through the vacuum delivery conduit 22 of FIG. 2, to draw a partial vacuum on the cavity 24, to urge the STFFM 70 further into the cavity 24, to the right of the vertical axis through the holes 27, 28. Then, the plunger 20 is actuated against the force of the spring 45, through engagement generally by the thumb of the surgeon, against the surface 21, such that the plunger 20 moves downwardly, bringing the needle 17 and its carried suture 18 downwardly, piercing the elastomeric sleeve 30, such the needle passes through the openings 27, 28, piercing the STFFM 70, as shown in FIG. 3c.

Because vacuum may be compromised when the needle pierces the sleeve 30, a clamping device 35 is also provided. The clamping device 35 is shown locked in the face-engaging position, with the clasp 43 locked against the keeper 44, such that the threaded member 40 may be rightwardly urged, by manually engaging the knob 42 and rotating the threaded member 40 in the threaded lower end of the member 35, such that its contact 41 engages the other surface 68 of the face, pushing the portion 70 of STFFM to the right thereof, into the cavity 24, in airtight engagement against the left-most end of the elastomeric sleeve 30. The clamping device 35 thus retains the status quo position of STFFM portion 70 in cavity 24 after vacuum is broken as the needle 17 pierces sleeve 30, in order to avoid STFFM movement as the needle 17 enters STFFM portion 70, that might otherwise result in needle breakage if the skin portion 70 moved while the needle is in engagement with the skin.

With reference now to FIG. 3d, it will be seen that the knob 33 is rotated in the direction of the arrow 60, such that the rod 32 connected to the knob 33 is likewise rotated, to turn the hook 31 from the non-engaged position thereof illustrated in FIG. 3c, to the suture-engaged position of FIG. 3d, in which it engages the loop of suture 18 that extends below the sleeve 30.

Then, as can be seen from FIG. 3e, the valve 20 can be actuated from outside by the surgeon, such that the vacuum is released, and the device 35 may be released by release of the clasp 43 from the keeper 44, and the suture-threaded portion of the STFFM 70 will remain connected to the lower end 13 of the insert, because the hook 31 remains in hooked relation to the loop of suture 18 shown beneath the sleeve 30, extending through the holes 27 and 28 even as the needle 17 is withdrawn from the position of the needle 17 shown in FIG. 3d, to its position as shown in FIG. 3e. Thus, the zone 70 of STFFM on the inside of outer STFFM layer 65, yet outside layer 66, remains connected to the lower end of the insert 10, for withdrawal therewith, when the insert 12 is raised in the direction of the arrow 80 of FIG. 3e, for removal of the insert 12 from the skin opening 11, whereby the facelift is effected.

With reference now to FIGS. 4a–4d, some of the finer points with respect to the formation of a loop for the suture 18, whereby the same may be engaged by a hook 31, will now be discussed.

With reference to FIG. 4a, it will be seen that the thumb "T" of the surgeon engages surface 21 of the plunger 20, driving the same downwardly, such that the leading protrusion 50 thereof, at the lower left end of the plunger 20 engages against and cams against the curved surface of the leaf spring 52, moving the same from the full line position therefore illustrated in FIG. 4a, to the phantom position therefore illustrated in FIG. 4a, against the action of compression spring 45, to drive the needle 17 downwardly, piercing the elastomeric sleeve 30 as described above, whereby the needle 17 may pierce the STFFM layer 65, carrying the suture 18 therewith.

Thus, the plunger 20 is moved from its position shown if FIG. 4a, to its position shown in FIG. 4b, in which the STFFM layer 65 is pierced, and in which the plunger 20 is in its downward position, with the leaf spring 52 having returned to its full line position from the phantom position therefor E illustrated in FIG. 4a.

With reference now to FIG. 4c, it will be seen that the thumb "T" of the surgeon has been removed, such that the compression spring 45 can urge the plunger 20 upwardly, such that the upper end of the protrusion 50 of the plunger 20 engages against the lower edge of the leaf spring 52, which limits the upper movement of the plunger 20 to an amount "D" as shown in FIG. 4c, whereby the needle 17 is carried upwardly by the plunger 20 the same amount "D", as the needle 17 moves from its phantom position therefore illustrated in FIG. 4c, to the full line position therefore illustrated in FIG. 4c, such that the suture 18 which is frictionally engaged with the STFFM layer 65 and elastomeric sleeve 30 against upward movement with the needle 18, forms a loop at its lower end as shown in FIG. 4c.

Then, the knob 33 is actuated as described above with respect to FIG. 3e, whereby the hook 31 engages the loop of the suture 18.

Next, the lever 54 is engaged by the forefinger "F" of the surgeon, depressing the same from its phantom position therefore illustrated in FIG. 4d, to its full line position therefore, whereby the short leg 39 of the lever pivots about the pivot point 55, to engage the cam 49 carried by the leaf spring 52, to cam the spring 52 leftwardly, from the full line position therefore illustrated in FIG. 4c, to the full line position illustrated therefore in FIG. 4d, to clear the passageway 51, such that the compression spring 45 may drive the plunger 20 upwardly, to return to its position shown in FIG. 4a, while withdrawing the needle 17 upwardly, out of the cavity 24, and removed from the skin layer 65 disposed therein, but with the suture 18 remaining in position through the skin layer 65, due to it being hooked by the hook 31 at its lower end as shown in FIG. 4d.

It will thus be seen that the vacuum lift feature of this invention enables the surgeon to engage STFFM internally of the patient, at a location on the STFFM that optimizes the engagement of the same with the needle and thread, with the ability to vary the precise location of engagement of the STFFM with the needle and thread for optimizing the lift of the STFFM. Then, in the case of, for example, a facelift, if the optimum engagement of STFFM occurs on one side of the face, the same, or mirror imaged location on the opposite side of the face may be engaged, with precision, to balance the lift effects on each side.

With specific reference now to FIG. 5, an alternative embodiment for the instrument 110 is illustrated in which in some situations, application of vacuum may not be necessary, by the use of a forceps, whereby a needle 117 is disposed within a sleeve 116, to be driven downwardly by a plunger (not shown) similar to the embodiment of FIG. 2, with the needle 117 carrying a suture 118. An external clamping device 135 similar to that of FIG. 2 is likewise carried by the instrument 110, having a clamp rod 138 that, in turn, carries a manual actuation knob 142 that is adapted to turn a threaded member 140, such that an exterior skin-engaging contact 141 is adapted to make contact with external skin 165, to urge the same into a cavity 124 that exists between a pair of cooperating toothed forceps 124, 125, mounted about a common pivot 126, which pivot 126, is, in turn, carried by a generally vertically disposed rod 112 that comprises part of the instrument 110. Thus, the toothed forceps 124, 125, may be lowered between skin layers of a face or the like similarly to the manner in which the insert 12 of FIG. 2 is used.

After the forceps 124, 125, are in place between inner and outer layers, the skin-contacting contact 141 will urge the skin 165 between the teeth 144, 145 of the forceps 124, 125, an amount such that the STFFM becomes disposed between the needle openings 127, 128 of the pincers 124, 125, such that downward movement of the needle 117 will carry the suture 118 through the openings 127, 128, whereupon the rod 113 that carries the hook 131 may be lowered to a position below the pincer 125, such that the hook 131 can engage a loop of the suture 118 in a manner similar to that described above with respect to FIGS. 4c and 4d.

It will be apparent that the rod 112 that carries the forceps 124, 125, may be unitary with the insert 110, even though the components of FIG. 5 are only fragmentally illustrated for the sake of clarity.

Also, with reference to FIG. 5a, an enlarged detail view of the forceps 124, 125 is fragmentally illustrated, including a device for controllably opening and closing the forceps 124, 125, comprising a threaded rod 170, carried for rotational movement from above (similar to that of the knob 33 of FIG. 3e), such that threads of the threaded rod 170 may be in engagement with comparably threaded portions of the forceps 124, 125, as shown in phantom at 171, 172, to urge the forceps 124, 125, more closely together, or farther apart, with such urging together being against the action of a leaf spring 173 disposed there between. It will be apparent that various other techniques for opening and closing the forceps 124, 125 may likewise be used, instead of the mechanism shown in FIG. 5a.

With reference now to FIG. 6, it will be seen that another alternative embodiment of the invention is disclosed, in which the needle 217 is essentially U-shaped at its lower end, adapted for movement upwardly in the direction of the arrow 219, to enter the openings 228, 227, such that the surgeon can manually recover the suture 218 with either a forceps (not shown), or a hook 231 carried by a rod 232, by directly observing the suture endoscopically. It will be understood that a protective chamber or cap like that 19 (not shown) of FIG. 2, may also be utilized to protect the needle and the patient at the lower end of the embodiment of FIG. 6. Such a chamber or safety cap is not shown in FIG. 6, for the sake of clarity of the rest of the items illustrated. It will further be understood that the various other components of the device of FIG. 6, numbered in the 200 series, correspond to similarly numbered items in FIGS. 2 and 2a carrying double digit numbers. Thus, item 212 of FIG. 6 corresponds to item 12 of FIGS. 2 and 2a; item 235 of FIG. 6 corresponds to item 35 of FIGS. 2 and 2a; chamber 224 of FIG. 6 corresponds to chamber 24 of FIGS. 2 and 2a, etc., such that redundant explanation of the operation of similar components of FIG. 6 to those of FIGS. 2 and 2a need not herein be repeated.

It will thus be seen that, while the operation of the instrument 10, 110 or 210 of this invention has been described above, by way of example, as being used to effect a facelift, the instrument 10, 110 or 210 can be used for various other purposes, where it is desired to engage STFFM inside an outer surface thereof, but outside an inner surface thereof, and to move that STFFM from one location to another, whether such lifting is upwardly, or in any other direction. Thus, the instrument of this invention may be used to effect brow surgery, a breast lift, a thigh lift, an abdominal skin lift, or any other shifting of STFFM from one location to another.

It will be understood that within the scope of this invention, various details may be modified, all within the spirit and scope of the invention as defined by the appended claims. For example, the threaded member 40 is shown by way of illustration only, in that any other contact member for engaging the outside surface of skin, to facilitate the placement of that portion of the STFFM that is to be sutured, may be effected. Accordingly, while a device of the type 35 that is shown for carrying the threaded member 40 may be of the type shown, various other techniques for engaging the outer surface 68 of skin may suffice. Similarly, while a clasp 43 may be used for locking the device 35 in a skin-contacting position as shown in FIG. 3d, any other form of locking device may likewise be utilized. Similarly, while an elastomeric cylindrical seal such as that 30 is shown for facilitating the maintenance of a vacuum around the outer surface of the needle 17 is shown as a preferred technique, various other vacuum-assuring techniques may alternatively be utilized. Also, while a hook such as that 31, actuable from a member such as that 33 is described as a means for securing the sutured STFFM 70 to the lower end 13 of the insert, other securement means may likewise be utilized. Furthermore, while the lever arrangement 54 and leaf spring 52 is shown as a means for holding the plunger 20 in the "down" position, various other techniques could likewise be used. Also, while the spring 45 is shown in the position for maintaining the plunger up, except when it is to be brought down against the force of the spring 45, the converse arrangement could be used, in which the spring generally maintains the plunger downward, until it is pulled upwardly.

It will be apparent from the foregoing that various other modifications and variations may be made in the instrument of this invention, all within the spirit and scope of the invention as defined in the appended claims.

What is claimed is:

1. An instrument for endoscopically, surgically engaging and grasping STFFM of a patient internally remote from a skin access opening and moving the engaged and grasped STFFM relative to the opening, comprising:
   (a) an elongate insert having first and second ends for insertion of the first end trough an incision or access opening in the STFFM of a patient to a location inside the skin of a patient that is remote from the incision or access opening, leaving the second end of the insert outside the incision or access opening;
   (b) means including a cavity at the first end of the insert, and partial vacuum delivery means applied via said insert, for delivering a partial vacuum to the cavity for engaging the STFFM in secured contact with said cavity at said first end of said insert internally of the outer surface of the skin and remote from the incision or access opening, with a partial vacuum delivery line provided to the instrument from the second end of the insert;
   (c) a suturing needle having first and second ends, carried by said insert and carrying a suture therewith;
   (d) means associated with said second end of said insert for actuating said first end of said needle for piercing the engaged STFFM of (b) above and passing the suture through the STFFM while the STFFM is in partial vacuum-drawn contact with said cavity;
   (e) means carried by the insert, cooperating with said first end of said needle for engaging and maintaining the suture through the portion of the engaged STFFM after withdrawal of the first end of the needle from the portion of the engaged STFFM;
   (f) means carried by the second end of the insert for engaging the second end of the needle and withdrawing the first end of the needle from the portion of the engaged STFFM;
   (g) whereby movement of the first end of the insert relative to the incision or access opening will cause the portion of the engaged STFFM internally of the outer surface of the skin to be correspondingly moved with the first end of the insert;

wherein said cavity has at least one hole therethrough for receiving the needle therein, with said hole additionally having sealing means for sealing against the needle when the needle passes into the cavity, to engage the STFFM, to maintain the partial vacuum seal between the cavity hole and the STFFM with the needle in engagement with the STFFM.

2. The instrument of claim 1, wherein the sealing means includes an elastomeric member disposed in contact with said cavity, for sealing around said needle when the needle penetrates the cavity, for maintaining the partial vacuum.

3. The instrument of claim 1 wherein the means for engaging and maintaining the suture of clause (c) of claim 1 comprises a hook means for hooking the suture.

4. The instrument of claim 3, wherein withdrawal means for withdrawing the needle are provided for effecting at least a partial withdrawal of the needle from the engaged STFFM, an amount sufficient to form a loop in the suture after the needle and suture have pierced the STFFM, whereby the hook means can engage the loop.

5. The instrument of claim 1 wherein the means for engaging and withdrawing of clause (f) of claim 1 comprises spring means biased for urging the suturing needle toward the second end of the insert.

6. The instrument of claim 1, wherein the cavity includes an STFFM-engaging opening facing toward the portion of the STFFM to be engaged.

7. The instrument of claim 6, wherein the cavity opening comprises means for effecting a vacuum seal of the STFFM disposed thereagainst.

8. The instrument of claim 1, wherein the insert is adapted for effecting a facelift, whereby the movement of clause (g) of claim 1 is adapted to lift the engaged portion of the STFFM toward the incision or access opening.

9. The instrument of claim 1, wherein the insert is adapted for any of:
   (a) brow surgery;
   (b) midface surgery; and
   (c) neck surgery.

10. The instrument of claim 1, wherein the instrument is adapted for effecting a breast lift.

11. The instrument of claim 1, wherein the instrument is adapted for effecting a thigh lift.

12. The instrument of claim 1, wherein the instrument is adapted for effecting any of:
   (a) an abdominal lift;
   (b) a buttocks lift and;
   (c) a muscular lift.

13. The instrument of claim 1, wherein the instrument is adapted for effecting an STFFM lift of fat from one location to another, on a patient.

14. The instrument of claim 1, wherein said instrument allows maximum flexibility for optimizing the location of engagement of the STFFM, for optimizing movement of the engaged STFFM.

15. An instrument for endoscopically, surgically engaging and grasping STFFM of a patient internally remote from a skin access opening and moving the engaged and grasped STFFM relative to the opening, comprising:
   (a) an elongate insert having first and second ends for insertion of the first end through an incision or access opening in the STFFM of a patient to a location inside the skin of a patient that is remote from the incision or access opening, leaving the second end of the insert outside the incision or access opening;
   (b) means including a cavity at the first end of the insert, and partial vacuum delivery means applied via said insert, for delivering a partial vacuum to the cavity for engaging the STFFM in secured contact with said cavity at said first end of said insert internally of the outer surface of the skin and remote from the incision or access opening, with a partial vacuum delivery line provided to the instrument from the second end of the insert;
   (c) a suturing needle having first and second ends, carried by said insert and carrying a suture therewith;
   (d) means associated with said second end of said insert for actuating said first end of said needle for piercing the engaged STFFM of (b) above and passing the suture through the STFFM while the STFFM is in partial vacuum-drawn contact with said cavity;
   (e) means carried by the insert, cooperating with said first end of said needle for engaging and maintaining the suture through the portion of the engaged STFFM after withdrawal of the first end of the needle from the portion of the engaged STFFM;
   (f) means carried by the second end of the insert for engaging the second end of the needle and withdrawing the first end of the needle from the portion of the engaged STFFM;
   (g) whereby movement of the first end of the insert relative to the incision or access opening will cause the portion of the engaged STFFM internally of the outer surface of the skin to be correspondingly moved with the first end of the insert;
wherein the means for engaging the STFFM in secured contact with said first end of said insert includes manual engagement means for manually engaging the outer surface of the skin when applied against the outside surface of the skin.

16. An instrument for endoscopically, surgically engaging and grasping STFFM of a patient internally remote from a skin access opening and moving the engaged and grasped STFFM relative to the opening, comprising:
   (a) an elongate insert having first and second ends for insertion of the first end through an incision or access opening in the STFFM of a patient to a location inside the skin of a patient that is remote from the incision or access opening, leaving the second end of the insert outside the incision or access opening;
   (b) means including a cavity at the first end of the insert, and partial vacuum delivery means applied via said insert, for delivering a partial vacuum to the cavity for engaging the STFFM in secured contact wit said cavity at said first end of said insert internally of the outer surface of the skin and remote from the incision or access opening, with a partial vacuum delivery line provided to the instrument from the second end of the insert;
   (c) a suturing needle having first and second ends, carried by said insert and carrying a suture therewith;
   (d) means associated with said second end of said insert for actuating said first end of said needle for piercing the engaged STFFM of (b) above and passing the suture through the STFFM while the STFFM is in partial vacuum-drawn contact with said cavity;
   (e) means carried by the insert, cooperating with said first end of said needle for engaging and maintaining the suture through the portion of the engaged STFFM after withdrawal of the first end of the needle from the portion of the engaged STFFM;
   (f) means carried by the second end of the insert for engaging the second end of the needle and withdrawing the first end of the needle from the portion of the engaged STFFM;
   (g) whereby movement of the first end of the insert relative to the incision or access opening will cause the portion of the engaged STFFM internally of the outer surface of the skin to be correspondingly moved with the first end of the insert;
wherein the cavity includes an STFFM-engaging opening facing toward the portion of the STFFM to be engaged, including wherein the means for engaging the STFFM in secured contact with said first end of said insert includes manual engagement means for manually engaging the outer surface of the skin when applied against the outside surface of the skin.

17. A surgical instrument comprising:
   (a) elongate insert means having first and second ends, for insertion of the first end into an incision or access opening of the skin between an outer surface thereof and STFFM that is inwardly of the outer skin surface to a location remote from the opening of the skin and with the second end of the insert means being located and operable outside the incision or access opening of the skin;
   (b) means on the first end of the insert means for engaging remote STFFM inwardly of the skin outer surface and for securing the remote STFFM to the first end of the insert, wherein the engaging and securing means includes means for suturing the remote STFFM to the first end of the insert, inwardly of the outer surface of the skin, wherein the engaging and securing means includes a suturing needle carried by the insert for entering the remote STFFM with a suture, and with a suture securing device separate from the needle and the suture being carried by the insert for engaging the suture after the suture passes through the STFFM, for securing the sutured remote STFFM to the first end of the insert upon actuation of the securing device from the second end of the insert, outside the incision or access opening in the skin;

(c) whereby withdrawal of the insert through the incision or access opening of the skin withdraws the remote engaged and secured STFFM toward the opening in the skin;

wherein the suture securing device comprises a hook means on the instrument for hooking the suture, outside the incision or access opening in the skin; including a cavity at the first end of the insert, wherein the engaging means includes partial vacuum engaging means delivering partial vacuum to the cavity at the first end of the insert, for sealingly engaging the remote STFFM in a partial vacuum seal in the cavity at the first end of the insert, wherein said cavity has at least one hole therethrough for receiving the needle therein, with said hole additionally having sealing means for sealing against the needle when the needle passes into the cavity, to engage the STFFM, to maintain the partial vacuum seal between the cavity hole and the STFFM with the needle in engagement with the STFFM.

18. A surgical instrument comprising;
(a) elongate insert means having first and second ends, for insertion of the first end into an incision or access opening of the skin between an outer surface thereof and STFFM that is inwardly of the outer skin surface to a location remote from the opening of the skin and with the second end of the insert means being located and operable outside the incision or access opening of the skin;
(b) means on the first end of the insert means for engaging remote STFFM inwardly of the skin outer surface and for securing the remote STFFM to the first end of the insert, wherein the engaging and securing means includes means for suturing the remote STFFM to the first end of the insert, inwardly of the outer surface of the skin, wherein the engaging and securing means includes a suturing needle carried by the insert for entering the remote STFFM with a suture, and with a suture securing device separate from the needle and the suture being carried by the insert for engaging the suture after the suture passes through the STFFM, for securing the sutured remote STFFM to the first end of the insert upon actuation of the securing device from the second end of the insert, outside the incision or access opening in the skin;
(c) whereby withdrawal of the insert through the incision or access opening of the skin withdraws the remote engaged and secured STFFM toward the opening in the skin;

wherein the engaging means includes clamp means carried by the insert for contacting an outer surface of the skin outside the remote STFFM and urging the remote STFFM against the first end of the insert.

19. A surgical instrument comprising;
(a) elongate insert means having first and second ends, for insertion of the first end into an incision or access opening of the skin between an outer surface thereof and STFFM that is inwardly of the outer skin surface to a location remote from the opening of the skin and with the second end of the insert means being located and operable outside the incision or access opening of the skin;
(b) means on the first end of the insert means for engaging remote STFFM inwardly of the skin outer surface and for securing the remote STFFM to the first end of the insert, wherein the engaging and securing means includes means for suturing the remote STFFM to the first end of the insert, inwardly of the outer surface of the skin, wherein the engaging and securing means includes a suturing needle carried by the insert for entering the remote STFFM with a suture, and with a suture securing device separate from the needle and the suture being carried by the insert for engaging the suture after the suture passes through the STFFM, for securing the sutured remote STFFM to the first end of the insert upon actuation of the securing device from the second end of the insert, outside the incision or access opening in the skin;
(c) whereby withdrawal of the insert through the incision or access opening of the skin withdraws the remote engaged and secured STFFM toward the opening in the skin;

wherein the engaging means includes partial vacuum engaging means delivered to the first end of the insert, for engaging the remote STFFM to the first end of the insert, and wherein the engaging means further includes clamp means carried by the insert for contacting an outer surface of the skin outside the remote STFFM and urging the remote STFFM against the first end of the insert.

20. The instrument of claim 19, wherein means are provided for effecting a partial withdrawal of the needle from the engaged STFFM, an amount sufficient to form a loop in the suture after the needle and suture have pierced the STFFM, wherein the suture securing means includes hook means for hooking the suture, whereby the hook means can engage the loop.

21. An instrument far endoscopically, surgically engaging and grasping STFFM of a patient internally remote from a skin access opening and moving the engaged and grasped STFFM relative to the opening, comprising:
(a) an elongate insert having first and second ends for insertion of the first end through an incision or access opening in the STFFM of a patient to a location inside the skin of a patient that is remote from the incision or access opening, leaving the second end of the insert outside the incision or access opening;
(b) means including a cavity at the first end of the insert, and partial vacuum delivery means applied via said insert, for delivering a partial vacuum to the cavity for engaging the STFFM in secured contact with said cavity at said first end of said insert internally of the outer surface of the skin and remote from the incision or access opening, with a partial vacuum delivery line provided to the instrument from the second end of the insert;
(c) a suturing needle having first and second ends, carried by said insert and carrying a suture therewith;
(d) means associated with said second end of said insert for actuating said first end of said needle for piercing the engaged STFFM of (b) above and passing the suture through the STFFM white the STFFM is in partial vacuum-drawn contact with said cavity;
(e) means carried by the insert, cooperating with said first end of said needle for engaging and maintaining the suture through the portion of the engaged STFFM after withdrawal of the first end of the needle from the portion of the engaged STFFM;
(f) means carried by the second end of the insert for engaging the second end of the needle and withdrawing the first end of the needle from the portion of the engaged STFFM;
(g) whereby movement of the first end of the insert relative to the incision or access opening will cause the portion of the engaged STFFM internally of the outer surface of the skin to be correspondingly moved with the first end of the insert;

wherein the cavity has at least one hole therethrough for receiving the needle therein, wherein the cavity includes an opening facing toward the portion of the STFFM to be engaged, wherein the cavity opening comprises means for effecting a partial vacuum seal of the STFFM disposed thereagainst, wherein the means for effecting the partial vacuum seal includes a rubber-like sealing member disposed over said hole of said cavity for effecting a sealing adherence to the needle after the needle passes through the hole in the cavity, for maintaining a partial vacuum on the STFFM engaged with the cavity opening.

* * * * *

UNITED STATES PATENT AND TRADEMARK OFFICE
CERTIFICATE OF CORRECTION

PATENT NO. : 7,060,079 B2
APPLICATION NO. : 10/336277
DATED : June 13, 2006
INVENTOR(S) : Allan E. Wulc and Stanley S. Wulc It is certified that error appears in the above-identified patent and that said Letters Patent is hereby corrected as shown below:

Column 9, line 61, delete--trough-- and insert -- through

Column 10, line 41, delete -- (c)-- and insert-- (e)

Column 14, line 28, delete -- far-- and insert -- for

Signed and Sealed this

Twelfth Day of September, 2006

JON W. DUDAS
*Director of the United States Patent and Trademark Office*